United States Patent [19]

Inoguchi et al.

[11] Patent Number: 4,865,910

[45] Date of Patent: Sep. 12, 1989

[54] GLASS FIBER PRODUCT FOR USE IN THE REINFORCEMENT OF FLUORORESIN

[75] Inventors: Hirokazu Inoguchi; Shoichi Watanabe, both of Fukushima, Japan

[73] Assignee: Nitto Boseki Co., Ltd., Japan

[21] Appl. No.: 275,226

[22] Filed: Nov. 22, 1988

[30] Foreign Application Priority Data

Nov. 26, 1987 [JP] Japan .................................. 62-298059

[51] Int. Cl.⁴ ........................ B32B 17/10; B32B 17/04
[52] U.S. Cl. .................................... 428/268; 428/289; 428/391; 428/404; 428/422; 428/429; 428/447
[58] Field of Search ............... 428/268, 289, 283, 404, 428/447, 391, 429, 422; 57/249, 250, 258; 65/3.1

[56] References Cited

U.S. PATENT DOCUMENTS

| | | | |
|---|---|---|---|
| 3,958,073 | 5/1976 | Trevisan et al. | 428/429 X |
| 4,711,820 | 12/1987 | Arkles et al. | 428/429 X |
| 4,749,610 | 6/1988 | Katsuragawa et al. | 428/268 X |
| 4,749,614 | 6/1988 | Andrews et al. | 428/268 X |

*Primary Examiner*—Thomas J. Herbert
*Attorney, Agent, or Firm*—Bert J. Lewen; Henry Sternberg; Beth Kovitz

[57] ABSTRACT

Here is disclosed a glass fiber product for use in the reinforcement of fluororesin which is improved in the adhesiveness to fluororesin. Thus, a glass fiber product for use in the reinforcement of fluororesin pre-treated with perfluoroalkylsilane represented by the following formula:

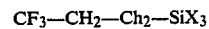

$$CF_3—CH_2—Ch_2—SiX_3$$

(X is a hydrolyzable group such as alkoxy groups having 1 to 4 carbon atoms) retains an excellent electrical insulation resistance.

5 Claims, No Drawings

GLASS FIBER PRODUCT FOR USE IN THE REINFORCEMENT OF FLUORORESIN

BACKGROUND OF THE INVENTION

1. Field of the Invention

The present invention relates to a glass fiber product for use in the reinforcement of fluororesin which is improved in adhesiveness to fluoroplastic.

2. Description of the Prior Art

Among the many thermoplastic materials, fluororesin is different from other plastic materials in that it has excellent heat resistance, chemical resistance and dielectric property. For this reason, fluoroplastic has been used in various fields.

Originally, fluororesin is a soft material. In order to compensate this softness, inorganic fillers such as glass fiber, graphite, molybdenum disulfide and the like are used. Among these inorganic fillers, glass fiber is most conventionally used in the field of electrical industry, because of its inexpensiveness and excellent electrical properties. Further, glass fiber greatly improves in the mechanical characteristics such as abrasion resistance, creep resistance, elastic modulus and the like. However, glass fiber is disadvantageous in that the minute gap formed at the interface between glass fiber and fluoroplastic brings about a deterioration in insulation resistance.

The problem of deterioration in insulation resistance makes the greatest trouble in expanding the use of a material in the field of electrical industry.

With the aim of overcoming this disadvantage, various attempts have been made up to today. They are:

(1) An attempt to use a glass fiber in the state of carrying greige goods on its surface, expecting that the interfacial adhesion will be improved owing to the baking effect (the so-called scorching) of the greige goods at the molding temperature of fluoroplastic (350° C. to 400° C.).

(2) An attempt to use greige goods of glass fiber in a state of appropriate scorching without burning them completely, expecting that the adhesion will be improved by the same effect as in (1).

(3) An attempt to apply the hitherto known general silane couplers (for example, a blend of silane couplers, a blend of a silane coupler and a primer such as silicone resin primer, fluororesin primer or the like, etc.).

However, none of these attempts could exhibit any significant effect.

The present inventors conducted many studies on the surface treatment of glass fiber for use in the reinforcement of fluororesin, with the aim of solving the above-mentioned problems.

SUMMARY OF THE INVENTION

It is the object of the present invention to provide a glass fiber for use in the reinforcement of fluororesin, which is improved in the adhesiveness to fluororesin.

The present invention provides a glass fiber product for use in the reinforcement of fluororesin which has been pre-treated with a perfluoroalkylsilane represented by the following formula:

$$CF_3-CH_2-CH_2-SiX_3$$

wherein X represents a hydrolyzable group such as alkoxy groups having 1 to 4 carbon atoms.

The present invention makes it possible to improve the adhesion of glass fiber to fluororesin to a great extent and to prevent the deterioration in insulation resistance.

DETAILED DESCRIPTION OF THE INVENTION

The perfluoroalkylsilanes which can be employed in the present invention include 3,3,3-trifluoropropyltrimethoxysilane, 3,3,3-trifluoropropyltriethoxysilane, 3,3,3-trifluoropropyltri(8-methoxyethoxy)silane, and the like. As the "X$_3$", —Cl$_3$ is also usable in place of said alkoxy groups having 1 to 4 carbon atoms.

The amount of perfluoroalkylsilane used in the invention varies depending on the kind of glass fiber product. However, it is usually 0.2 to 3.0% (by weight, hereinafter the same) and preferably 0.5 to 2.0%, as expressed in terms of the concentration of treating solution. Further, its amount is usually 0.06 to 0.50% and preferably 0.10 to 0.35%, as expressed in terms of the amount attached to glass fiber. In carrying out the surface treatment, some contrivance, such as making the perfluoroalkylsilane into a solution in an organic solvent, or the like, is necessary, because these perfluoroalkylsilanes are relatively poor in water-solubility. At this time, pH must be 4 or below, and preferably in the range of 2 to 4. As the organic solvent, methanol is particularly preferable. Concentration of the organic solvent in the solution is preferably 30 to 40% by weight. Ordinary surface treatment process for glass fibers, by any of the techniques known to the art, such as dipping, roll coating, or spraying, etc., may be adopted in the invention.

As the glass fiber usable in the invention, E glass (non-alkali glass for electrical use), S glass (high strength glass), D glass (low dielectric constant glass), quartz glass, A glass (acid resistant glass), C glass (alkali-containing glass for chemical use), and the like can be referred to.

As the glass fiber product, glass fabric, glass tape, glass yarn, glass mat, glass paper, glass powder and the like can be referred to.

Although there are known several kinds of perfluoroalkylsilane compounds resembling the perfluoroalkylsilane used in the present invention, they are all unsatisfactory from the viewpoint of production process, cost, water-solubility at the time of surface treatment, effect as a surface treating agent, etc. For example, perfluoroalkylsilanes represented by the following formulas:

$$CF_3(CF_2)_5CH_2CH_2Si(OMe)_3$$

$$CF_3(CF_2)_7CH_2CH_2Si(OMe)_3$$

$$CF_3(CF_2)_7CH_2CH_2SiMe(OMe)_3$$

lack water-solubility and surface treatment with their methanolic solutions exhibit no effect.

At the time of surface treatment, some additives (surfactant, other silane coupler, etc.) may be added to the surface treating solution for the purpose of increasing the flexibility of glass fiber and thereby promoting the physical permeation of tetrafluorocarbon resin into the intersticss of glass fiber filaments.

Said perfluoroalkylsilane is excellent in affinity and compatibility with fluororesin. According to the invention, the surface of glass fiber product is treated with such a perfluoroalkylsilane, and thereby affinity and adhesiveness between glass fiber product and fluororesin are improved.

(1) The organic functional group (CF$_3$CH$_2$CH$_2$) of the perfluoroalkylsilane (CF$_3$CH$_2$CH$_2$-SiX$_3$) takes part in the affinity and adhesion with fluororesin. Further, an inter-polymer network (I. P. N.) seems to be formed between fluororesin and the molecular chain of the organic functional group moiety.

(2) The hydrolyzable group X of the silane compound is hydrolyzed under specified conditions (at a pH value of 4 or below, etc.) in order that the glass fiber surface treated with the perfluoroalkylsilane exhibits sufficient adhesiveness or bonding force, and the resulting silanol group forms a siloxane linkage with the glass surface.

The effect of the invention is exhibited by the above-mentioned mechanism. Regarding the affinity and adhesion between perfluoroalkylsilane and fluoroplastic mentioned in paragraph (1), occurrence of the following phenomenon is also assumable, in addition. That is, in the high temperature process at 350° C. to 400° C., a part of the fluoroplastic forms radicals which cause a crosslinking reaction.

The perfluoroalkylsilane takes part in this reaction at least partially. Due to this reaction in addition to the I. P. N., it forms a linkage with fluororesin.

(PRACTICAL EXAMPLES)

Example 1

1) Treating solution

| | |
|---|---|
| 3,3,3-Trifluoropropyltriethoxysilane (FTS-E manufactured by Chisso K.K.) | 1.0% |
| Acetic acid | 0.2% |
| Methyl alcohol | 30.0% |
| Water | 68.8% |
| Total | 100% |

2) Glass fabric

WE-116$^E$ (a glass fiber fabric manufactured by Nitto Boseki K.K.) was degreased by heat cleaning and put to use. 3) Surface treatment The glass fabric of 2) was dipped into the treating solution of 1) and squeezed by means of squeezing roll. Then, it was dried in an oven at 110° C. for 5 minutes. 4) Preparation of laminate A surface-treated glass fabric was dipped in a tetrafluoroethylene resin dispersion (Teflon 30-J, manufactured by Mitsui Fluorochemical K.K.) and air-dried, after which it was dried at 370° C. for 2 minutes.

This procedure was repeated twice to obtain a prepreg having a resin content of 55%.

Sixteen sheets of the prepreg were stacked. After superposing a copper foil (35 μm in thickness) on its both sides, the whole was compression molded at 400° C. under a pressure of 50 kg/cm$^2$ for 60 minutes to prepare a copper foil-lined laminate. 5) Testing method Electrical insulation resistance was measured according to the testing method of JIS-C-6481, after boiling test piece at 100° C. for 2 hours.

Example 2

1) Treating solution

| | |
|---|---|
| 3,3,3-Trifluoropropyltrimethoxysilane (XC95-418, manufactured by Toshiba Silicone K.K.) | 1.0% |
| Acetic acid | 0.2% |
| Methyl alcohol | 30.0% |
| Water | 68.8% |
| Total | 100% |

The other conditions were the same as in Example 1.

Comparative Example 1

As the glass fabric, WE 116$^E$ not subjected to heat cleaning and carrying a greige good was used.

Comparative Example 2

As the glass fabric, WE 116$^E$ which had been subjected only to a preliminary degreasing at 400° C. for 20 to 30 seconds until the greige good was appropriately scorched was used.

Comparative Example 3

General silane coupler blend

As the glass cloth, WE 116$^E$ which had been degreased by heat cleaning and then treated with a treating solution having the following formulation was used.

Phenyltrimethoxysilane

| | |
|---|---|
| (AX43-040, manufactured by Toray Silicone K.K.) | 0.8% |
| γ-(2-Aminoethyl)-aminopropyl-trimethoxysilane NH$_2$CH$_2$CH$_2$NHCH$_2$CH$_2$CH$_2$Si(OCH$_3$)$_3$ (SH 6020 manufactured by Toray Silicone K.K.) | 0.2% |
| Acetic acid | 2.0% |
| Water | 97.0% |
| Total | 100% |

Comparative Example 4

A perfluorosilane CF$_3$(CF$_2$)$_5$CH$_2$CH$_2$Si(OCH$_3$)$_3$ (3,3-4,4-5,5-6,6-7,7-8,8,8-trideaafluorooctyltrimethoxysilane (XC95-468, manufactured by Toshiba Silicone K.K.), i.e. a perfluorosilane resembling the perfluorosilane of the present invention in structure, was used in the surface treatment.

| | |
|---|---|
| XC95-468 | 1.0% |
| Methanol | 95.0% |
| Water | 3.5% |
| Acetic acid | 0.5% |
| Total | 100% |

The samples of Examples 1 and 2 and Comparative Examples I to 4 were examined for electrical insulation resistance. The results are summarized in Table 1.

TABLE 1

| | Example | | Comparative Example | | | |
|---|---|---|---|---|---|---|
| | 1 | 2 | 1 | 2 | 3 | 4 |
| Surface | 3,3,3-Tri- | 3,3,3-Tri- | Greige | Preliminary | Blend of | Perfluoro- |

TABLE 1-continued

|  | Example 1 | Example 2 | Comparative Example 1 | Comparative Example 2 | Comparative Example 3 | Comparative Example 4 |
|---|---|---|---|---|---|---|
| treatment agent and the others | propyltri-ethoxy-silane 1.0% solution | fluoropropyl-trimethoxy-silane 1.0% solution | good of glass fiber | degreasing of greige good of glass fiber | general silane couplers | resembling that of this invention (3,3-4,4-5,5-6 6-7,7-8,8,8-tridecafluoro-octyltrimethoxy-silane) 1.0% solution |
| Amount of treating agent attached (%) | 0.16 | 0.14 | 3.2* | 0.28* | 0.14 | 0.14 |
| Thickness of laminate (mm) | 1.56 | 1.57 | 1.60 | 1.57 | 1.57 | 1.60 |
| Electrical insulation resistance (ohms after boiling at 100° C. for 2 hrs.) | $2.4 \times 10^{13}$ | $1.2 \times 10^{13}$ | $<10^9$ | $<10^9$ | $5.1 \times 10^{10}$ | $5.5 \times 10^{10}$ |

*Not containing coupling agent.

Effect of the Invention

A fluoroplastic molding material filled and reinforced with the glass fiber product of the invention is not only improved in abrasion resistance, creep resistance and elastic modulus, but also markedly prevented from the deterioration of insulating resistance which is a side effect having been unavoidable according to the prior techniques.

Particularly, the printed circuit board made of fluoroplastic reinforced with the glass fabric of the invention shows only a small deterioration in insulation resistance after being boiled, so that its usefulness is very high and it is adoptable in the field of multi-layered print circuit board where this type of products have hitherto been unemployable because of deterioration in insulation resistance.

What is claimed is:

1. A glass fiber product for use in the reinforcement of fluororesin which is pre-treated with perfluoroalkyl-silane represented by the following formula:

$$CF_3-CH_2-CH_2-SiX_3$$

wherein X represents a hydrolyzable group such as alkoxy groups having 1 to 4 carbon atoms.

2. A glass fiber product for use in the reinforcement of fluororesin according to claim 1, wherein said glass fiber product is a glass fabric, a glass tape, a glass yarn, a glass mat, a glass paper or a glass powder.

3. A glass fiber product for use in the reinforcement of fluororesin according to claim 1, wherein said perfluoroalkylsilane is 3,3,3-trifluoropropyltrimethoxysilane, 3,3,3-trifluoropropyltriethoxysilane or 3,3,3-trifluoropropyltri(8-methoxyethoxy)silane.

4. A glass fiber product for use in the reinforcement of fluororesin according to claim 1, wherein said perfluoroalkylsilane is attached to the glass fiber in an amount of 0.06 to 0.50% by weight.

5. A glass fiber product for use in the reinforcement of fluororesin according to claim 1, wherein X in said formula is a —Cl group.